(12) United States Patent
Cardelius et al.

(10) Patent No.: US 7,063,668 B2
(45) Date of Patent: Jun. 20, 2006

(54) METHOD AND ARRANGEMENT FOR ACOUSTIC DETERMINATION OF MOISTURE CONTENT OF A GAS MIXTURE

(75) Inventors: Erik Cardelius, Stockholm (SE); Åke Larsson, Järfälla (SE); Lars Skoglund, Sollentuna (SE)

(73) Assignee: Maquet Critical Care AB, Solna (SE)

( * ) Notice: Subject to any disclaimer, the term of this patent is extended or adjusted under 35 U.S.C. 154(b) by 16 days.

(21) Appl. No.: 10/823,444

(22) Filed: Apr. 13, 2004

(65) Prior Publication Data

US 2004/0211244 A1   Oct. 28, 2004

(30) Foreign Application Priority Data

Apr. 28, 2003   (SE)   .................... 0301226

(51) Int. Cl.
*A61B 5/00*   (2006.01)
(52) U.S. Cl. ................. 600/532; 600/529; 122/204.22; 73/23.2; 73/29.01
(58) Field of Classification Search ................. 73/23.3; 128/204.22
See application file for complete search history.

(56) References Cited

U.S. PATENT DOCUMENTS

| | | | |
|---|---|---|---|
| 4,280,183 A * | 7/1981 | Santi | ............................ 702/24 |
| 4,520,654 A | 6/1985 | Terhune | |
| 4,581,942 A * | 4/1986 | Ogura et al. | ............. 73/861.04 |
| 4,876,889 A | 10/1989 | Shakkottai et al. | |
| 5,351,522 A * | 10/1994 | Lura | ......................... 73/24.01 |
| 5,581,014 A * | 12/1996 | Douglas | .................... 73/24.01 |
| 5,645,071 A | 7/1997 | Harnoncourt et al. | |
| 5,915,834 A * | 6/1999 | McCulloh | ................. 366/151.1 |

FOREIGN PATENT DOCUMENTS

| | | |
|---|---|---|
| DE | 3215534 A1 * | 11/1982 |
| EP | 1 205 748 | 5/2002 |
| WO | WO 99/67649 | 12/1999 |

\* cited by examiner

*Primary Examiner*—Robert L. Nasser
*Assistant Examiner*—Patricia Mallari
(74) *Attorney, Agent, or Firm*—Schiff Hardin LLP

(57) ABSTRACT

A mechanical breathing aid has first and second inlets respectively connectable to a source of air and a source of oxygen. A mixing location is in gaseous communication with the first and second inlets, at which controlled amounts of air and oxygen from the respective inlets are mixed. An acoustic analyzer operates during a measurement procedure to access a moisture content value for air from the source of air, to generate acoustic velocity-related information from acoustic energy interaction with the breathing gas, and to determine therefrom an oxygen content. The analyzer operates during a calibration procedure to generate acoustic velocity-related information from acoustic energy interaction with air from the source of air, and to determine therefrom an oxygen content value for the air from which is determined a moisture content value for air.

4 Claims, 2 Drawing Sheets

METHOD AND ARRANGEMENT FOR ACOUSTIC DETERMINATION OF MOISTURE CONTENT OF A GAS MIXTURE

BACKGROUND OF THE INVENTION

1. Field of the Invention

The present invention relates to a method and a device for acoustic determination of the moisture content of a multiple gas component gas mixture and in particular to a method and device employing acoustic velocity related measurements in the determination.

2. Description of the Prior Art

In medical applications involving the supply of a breathing gas to a patient, pressurized air and oxygen are often mixed to attain an essentially binary component (oxygen/nitrogen) breathing gas mixture having a desired therapeutic oxygen content. This mixing is often carried out within a mechanical breathing aid, such as a ventilator, respirator or inhalation anaesthetic delivery system, which is designed to also control the subsequent delivery of the mixed breathing gas to a patient. The composition of the breathing gas requires close monitoring and it is well known to employ an acoustic, typically an ultrasonic, analyzer connectable to or integral with the mechanical breathing aid for this purpose. Additionally, it may be desirable to monitor the moisture content of the breathing gas so as to avoid dehydration of a patient receiving the gas, which may occur if a dry breathing gas were provided.

Known acoustic analyzers generally have an acoustic, typically ultrasonic, arrangement devised to emit acoustic energy into and detect acoustic energy from an acoustic path within the breathing gas, and to generate from this an output signal containing acoustic velocity $V_S$ related information. A signal processor receives the acoustic velocity related information and determines therefrom the composition of the binary gas mixture according to the known equation:

$$V_S = \left(\frac{C_P^* R_M T}{C_V^* M^*}\right)^{\frac{1}{2}} \quad (1)$$

wherein T is the absolute temperature (Kelvin) of the gas; $R_M$ is the universal gas constant; and $C^*_P$, $C^*_V$ and $M^*$ are respectively the specific heat capacity at constant pressure, the specific heat capacity at constant volume and the molecular weight of the binary breathing gas mixture, and are given by:

$$C_P^* = \frac{C_{P1} M_1 x_1 + C_{P2} M_2 x_2}{M_1 x_1 + M_2 x_2} \quad (2)$$

$$C_V^* = \frac{C_{V1} M_1 x_1 + C_{V2} M_2 x_2}{M_1 x_1 + M_2 x_2} \quad (3)$$

$$M^* = M_1 x_1 + M_2 x_2 \quad (4)$$

wherein the subscripts 1 and 2 refer to a gas 1 and a gas 2 of the binary gas mixture and $x_i$ is the fraction of the respective gas in the mixture so that $$x_1 + x_2 = 1 \quad (5)$$

The pressurized oxygen source connected to such a breathing aid typically originates from an external supplier and has negligible moisture content. The pressurized air, however, normally is generated on-site and is made available at the breathing aid either from an attendant compressor or from a wall outlet connected to a central compressor located within the medical facility. A problem is that this pressurized air normally contains an unknown, small but significant amount of moisture. This moisture may be considered as a third gas (gas 3), component of the breathing gas mixture and can lead to errors in the determination of the composition of the breathing gas which is based on the equations (1)–(5) above.

Including this third gas in the equations (2)–(5) gives:

$$C_P^* = \frac{C_{P1} M_1 x_1 + C_{P2} M_2 x_2 + C_{P3} M_3 x_3}{M_1 x_1 + M_2 x_2 + M_3 x_3} \quad (2')$$

$$C_V^* = \frac{C_{V1} M_1 x_1 + C_{V2} M_2 x_2 + C_{V3} M_3 x_3}{M_1 x_1 + M_2 x_2 + M_3 x_3} \quad (3')$$

$$M^* = M_1 x_1 + M_2 x_2 + M_3 x_3 \quad (4')$$

and $$x_1 + x_2 + x_3 = 1 \quad (5')$$

Since the fraction of moisture, $x_3$, in the mixture changes as the $O_2$ fraction changes and assuming all moisture in the mixture comes from the air (gas 1) then:

$$x_3 = k(1 - x_2) \quad (6')$$

where k is the moisture fraction of the air before mixing.

In order to reduce these errors it is known to determine the volume fraction (here $x_3$) of moisture (gas 3) within the breathing gas mixture other than by employing the acoustic analyzer, such as by using a known moisture sensor, and then to insert the measured value into the equations (2')–(6'). The composition of the "binary" gas breathing gas mixture can then be determined using the acoustic analyzer.

The addition of a dedicated moisture sensor adds expense and complexity to the analyzer. To avoid these problems with the inclusion of a moisture sensor, an estimation of a probable value for the volume fraction of moisture can be made without measurement and entered into the equations (2')–(6') as a constant for use within the acoustic analyser in the determination of the compositional information.

SUMMARY OF THE INVENTION

It is an object of the present invention to provide a method and an arrangement for the acoustic determination of the moisture content of a gas mixture, wherein fewer components are required than in conventional methods and arrangements.

This object is achieved in accordance with the principles of the present invention in a method and a breathing aid wherein first and second inlets are respectively connectable to a source of air and a source of oxygen, a mixing location is in gaseous communication with the first and second inlets at which controlled amounts of air and oxygen from the respective inlets are mixed, and wherein an acoustic analyzer is operated during a measurement procedure to access a moisture content value for the air from the source of air and to generate acoustic velocity-related information from the interaction of acoustic energy with the breathing gas, and to determine therefrom an oxygen content. The analyzer further operates, during a calibration procedure, to generate acoustic velocity-related information from the interaction of acoustic energy with the air from the source of air and to determine therefrom an oxygen content value for the air, from which a moisture content value for the air is determined.

By providing an analyzer which, during a calibration phase, can operate to make an acoustic determination of the moisture content of the air being supplied to form the breathing gas mixture, the need for a separate moisture sensor is avoided while still allowing an actual measurement of the moisture content to be employed in subsequent compositional information determinations.

Oxygen, being also supplied to form the breathing gas mixture, may also be provided separately during the calibration phase and the analyzer can operate to determine a calibration value from acoustic velocity measurements made therein to compensate within the analyser for errors not related to changes in the gas mixture.

Moreover, the analyzer can operate to generate a warning signal if the calculated value for the moisture content indicates an abnormally low or, particularly, an abnormally high moisture level in the air being supplied to the mechanical breathing aid.

DESCRIPTION OF THE PREFERRED EMBODIMENTS

Figure 1:
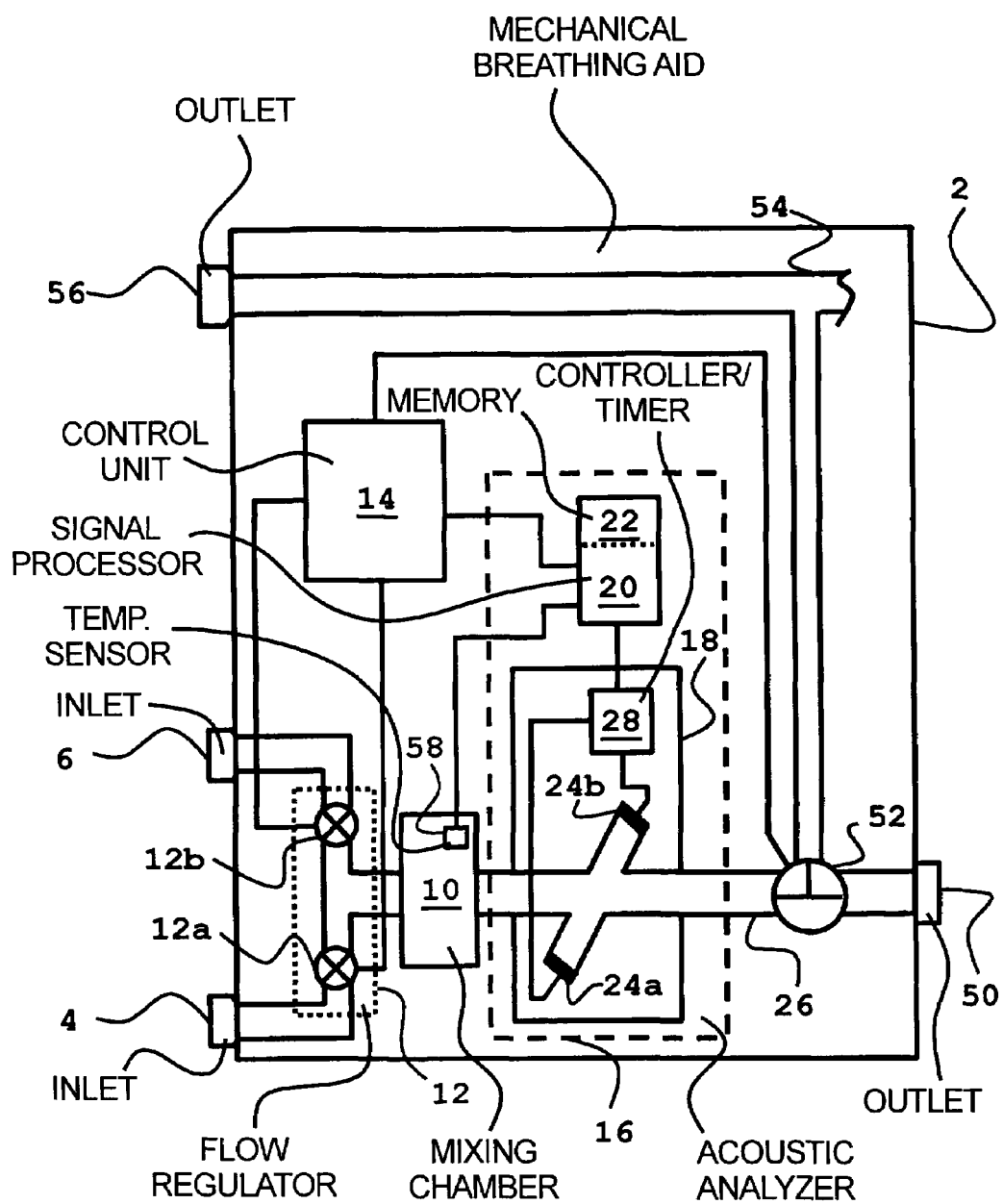
FIG. 1 is a schematic diagram of a mechanical breathing aid according to the present invention.

FIG. 1 illustrates a mechanical breathing aid 2 that is described below only in the detail necessary for an understanding of the invention. It will be appreciated that functions and components not described below, but which are typically found in mechanical breathing aids, may be included within the breathing aid 2 but are not essential to the invention.

The mechanical breathing aid 2 has a first inlet 4, connectable to a source of one or the other of pressurized air and pressurized oxygen (not shown), and a second inlet 6 connectable to the other of the pressurized air or oxygen sources (not shown). A mixing chamber 10 is provided in gaseous communication with each of the first inlet 4 and the second inlet 6 via a controllable flow regulator 12, such as may be formed using flow control valves 12a, 12b respectively coupled to the inlets 4, 6, which is adjustable to vary the relative amounts of the gases from the inlets 4, 6 entering the mixing chamber 10. A microprocessor-based control unit 14 is arranged in operable connection with the flow regulator 12 and generates a control signal for use by the flow regulator 12 to establish a desired binary breathing gas mixture within the mixing chamber 10. In the present embodiment the controller 14 also is arranged in operable connection with a flow direction controller 52 which is movable in response to a control signal therefrom between a first position in which gas from the mixing chamber 10 is able to flow to a supply outlet 50, and a second position in which gas from the chamber 10 enters an exhaust line 54 to be removed from the breathing aid 2 via an exhaust outlet 56.

An acoustic analyzer 16 generates acoustic velocity-related information from acoustic energy hat interacts with the binary gas, for example at a location downstream of the mixing chamber 10, and determines therefrom an oxygen content value for the binary gas for use by the control unit 14 in the generation of the control signal. A temperature sensor 58, here located in thermal contact with gas in the mixing chamber 10, is provided to generate a signal indicative of the gas temperature T at the acoustic analyzer 16.

The acoustic analyzer 16 includes an ultrasonic arrangement 18 and a signal processor 20 which has an internal random access memory (RAM) 22. The ultrasonic arrangement 18 of the present embodiment has a pair of ultrasonic transducers 24a, 24b, and a transducer controller/timer 28 in operable connection with the transducers 24a, 24b. The transducers 24a, 24b are here disposed opposing one another to delimit an ultrasound path which traverses a gas conduit 26 connected to internal the mixing chamber 10, for example, at an angle to the gas flow direction within the conduit 26. This configuration of transducers 24a, 24b which is used in the present embodiment is well known and is preferentially employed to facilitate an additional gas flow measurement with the ultrasonic arrangement 18.

The controller/timer 28 is designed to operate one transducer of the pair (such as 24a) to emit an ultrasound pulse along the ultrasound path and to operate the other one of the pair (24b) to generate a signal indicative of the arrival of the so emitted pulse after its interaction with gas within the conduit 26. A microprocessor (not shown) within the controller/timer 28 is programmed to determine from the generated signal a transit time t for the ultrasound along the length L of the ultrasound path, and from this to determine a velocity value $V_S$ for ultrasound in the gaseous medium within the conduit 26 using an algorithm based on the equation:

$$V_S = L/t \qquad (7)$$

The signal processor 20 receives this velocity value $V_S$ and is programmed to determine compositional information for the gaseous medium using algorithms based on the equations (1) and (2–5) or (2'–6'), as appropriate and, in the present embodiment, the value of the temperature T from the sensor 58.

Figure 2:
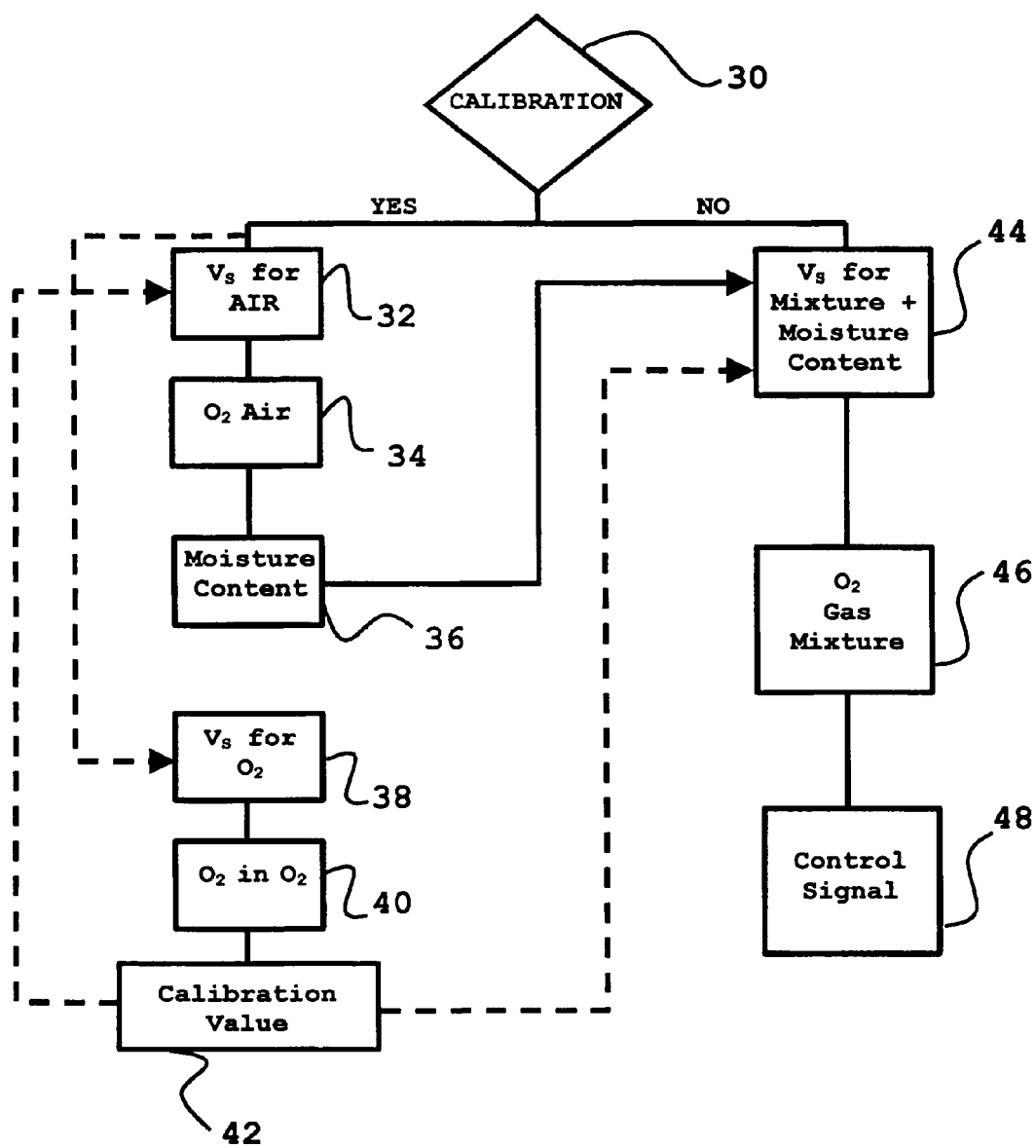
FIG. 2 is a flow chart of a method for operating an acoustic analyzer according to the invention utilized in the breathing aid of FIG. 1.

Considering now the operational flow chart that is illustrated in FIG. 2 for the acoustic analyzer 16, in the present embodiment a determination is made at step 30 as to whether the mechanical breathing aid 2 is in a calibration procedure (YES) or a measurement procedure (NO). This can be done, for example, by the control unit 14 checking for a user input signifying a start of a calibration procedure and then emitting a signal to the signal processor 20 indicative of this. Alternatively, for example, a calibration procedure may be entered automatically at the start up of the breathing aid 2 and/or at predetermined time intervals during its use, or some combination of the two may be used.

Regardless of how the determination is made at step 30, upon entering a calibration procedure the control unit 14 controls the flow regulator 12 to allow passage of only air from the associated inlet 4 or 6, through the mixing chamber 10 and to the acoustic analyser 16 where, at step 32, a velocity value for ultrasound in the air is generated within the controller/timer 28. From this velocity value at step 34 the signal processor 20 is programmed to calculate an oxygen concentration value based on the equations (1) and (2'–5'), assuming air to be a gas mixture of nitrogen, oxygen. In the present embodiment, at step 36, the signal processor 20 is further programmed to calculate a value for the moisture content of the air from a deviation between the previously calculated oxygen content and an expected oxygen content (20.9% for dry air the value of which may be stored in the RAM 22) and to store this value for the moisture content in the RAM 22. This may be done iteratively by adjusting the value of k in equation (6') until the calculated value of oxygen concentration equals the expected value of here 20.9%.

Additionally, the signal processor 20 can be programmed to compare the thus-calculated moisture content value with one or both upper and lower limit values and to generate a warning signal if the so calculated value lies outside one or the other limit.

In an optional refinement to this procedure, illustrated by the broken line path in FIG. 2, a calibration value may be calculated preferably, but not essentially, before the determination of the velocity value for ultrasound in air at step 32. In this procedure the control unit further controls the flow regulator 12 to allow passage of only the dry oxygen from the other inlet 4 or 6, through the mixing chamber 10 and to the acoustic analyser 16. The acoustic analyzer 16 operates to determine a value for the oxygen concentration (step 40) from equation (1) using ultrasonic velocity measurements in the oxygen (step 38) and to then calculate a calibration value based on a deviation of the determined oxygen concentration from the expected concentration (100% for dry oxygen). This calibration value may then be used within the signal processor 20 to compensate subsequent compositional information calculations, made during the calibration or measurement procedures, for errors which are unrelated to gas compositional changes, such as errors in the value of the length L of the ultrasound path between the transducer pair 24a, 24b.

After a calibration procedure, as described above, has been undertaken the moisture content value for the air being used within the mechanical breathing aid 2 is available for use during compositional information calculations which will be made during subsequent measurement procedures. Thus, if at step 30 it is determined that a measurement procedure is required (NO), that is the controller 14 of the mechanical breathing aid 2 is operating to generate an oxygen/air breathing gas mixture within the mixing chamber 10, then the acoustic analyser 16 of the present embodiment is configured to operate according to the process steps 44, 46 and 48 which are illustrated in the FIG. 2. During the measurement procedure the ultrasonic arrangement 18 is operated to obtain ultrasonic velocity information for the gas mixture and to provide this to the signal processor 20 which is programmed to access and retrieve the moisture content value that is stored in the RAM 22 (step 44). The signal processor 20 is programmed to then calculate an oxygen content value for the gas mixture based on an algorithm using the equations (1) and (2'–6') as necessary and the velocity and moisture content values (step 46). The signal processor 20 is configured to then generate a control signal which contains the so calculated oxygen content value (step 48) for use by the controller 14 in establishing a desired gas mixture for supply from the breathing aid 2 through an outlet 50.

It will be appreciated that the inclusion of a dedicated signal processor 20 enhances the flexibility of the analyzer 16, making it a stand-alone component that can be used in a variety of situations but that, without departing from the inventive concept, some or all of its functionality may be included in a suitably programmed controller 14 to make the analyser a machine-specific component at a reduced element cost.

Although modifications and changes may be suggested by those skilled in the art, it is the intention of the inventors to embody within the patent warranted hereon all changes and modifications as reasonably and properly come within the scope of their contribution to the art.

We claim:

1. A method for determining a moisture content of air comprising the steps of:
   during a calibration procedure, introducing an air sample into an acoustic analyzer;
   in said acoustic analyzer, interacting acoustic energy with the air sample to obtain acoustic velocity-related information from the air sample;
   in said acoustic analyzer, determining compositional information for at least one of oxygen and nitrogen in said air sample using said acoustic velocity-related information;
   in said acoustic analyzer, determining a deviation of said compositional information from expected compositional information for dry air;
   during a measurement procedure following said calibration procedure, introducing an oxygen/air gas sample into the acoustic analyzer;
   in said acoustic analyzer, interacting acoustic energy with the oxygen/air gas sample to generate further acoustic velocity-related information for said oxygen/air gas sample;
   in said acoustic analyzer, determining further compositional information for an oxygen content of said oxygen/air gas sample using said further acoustic velocity-related information and said moisture content value calculated for said air sample; and
   in said acoustic analyzer, calculating a moisture content value for the air sample from said deviation.

2. A method as claimed in claim 1 comprising, in said calibration procedure:
   introducing a sample of said dry gas into said acoustic analyzer, said dry gas sample having a known composition of at least one constituent gas;
   in said acoustic analyzer, interacting acoustic energy with said sample of said dry gas for obtaining further acoustic velocity-related information for said sample of said dry gas;
   in said acoustic analyzer, determining further compositional information for said at least one constituent gas in said sample of said dry gas using said further acoustic velocity-related information; and
   in said acoustic analyzer, calculating a calibration value dependent on a deviation of said further compositional information from said known composition, and using said calibration value in the calculation of said moisture content value.

3. A method as claimed in claim 2 wherein the step of introducing a sample of said dry gas into the acoustic analyzer comprises introducing oxygen into the acoustic analyzer as said sample of said dry gas.

4. A mechanical breathing aid comprising:
   a first inlet adapted for connection to a source of air;
   a second inlet adapted for connection to a source of oxygen;
   a mixing location in gaseous communication with said first and second inlets at which controlled amounts of air and oxygen from the respective first and second inlets are mixed to form a breathing gas; and
   an acoustic analyzer having access to a moisture content value for air from said source of air, said acoustic analyzer emitting acoustic energy into said breathing gas and, from interaction of said acoustic energy with said breathing gas, obtaining acoustic velocity-related information from said breathing gas, said acoustic analyzer determining an oxygen content value of said breathing gas from said acoustic velocity-related information, and, during a calibration procedure, obtaining further acoustic velocity-related information by interacting acoustic energy with air from said source of air and, from said further acoustic velocity-related information, determining an oxygen content value for the air and, from said oxygen content value for the air, calculating the moisture content value for the air.

* * * * *